United States Patent
Suon et al.

(10) Patent No.: US 6,342,062 B1
(45) Date of Patent: Jan. 29, 2002

(54) RETRIEVAL DEVICES FOR VENA CAVA FILTER

(75) Inventors: Naroun Suon, Lawrence; James Weldon, Roslindale, both of MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/404,116

(22) Filed: Sep. 23, 1999

Related U.S. Application Data

(60) Provisional application No. 60/101,616, filed on Sep. 24, 1998.

(51) Int. Cl.[7] .................................................. A61F 2/02
(52) U.S. Cl. ...................................................... 606/200
(58) Field of Search .............................. 606/200, 113, 606/205–206, 114, 127; 604/104; 623/1

(56) References Cited

U.S. PATENT DOCUMENTS

| | | | | |
|---|---|---|---|---|
| 3,952,747 A | * | 4/1976 | Kimmell, Jr. | 128/303 |
| 4,425,908 A | * | 1/1984 | Simon | 128/303 |
| 4,643,184 A | * | 2/1987 | Mobin-Uddin | 128/303 |
| 4,832,055 A | * | 5/1989 | Palestrant | 128/899 |
| 4,990,156 A | * | 2/1991 | Lefebvre | 606/200 |
| 4,994,079 A | * | 2/1991 | Genese et al. | 606/206 |
| 5,108,406 A | * | 4/1992 | Lee | 606/106 |
| 5,147,379 A | * | 9/1992 | Sabbaghian et al. | 606/200 |
| 5,171,233 A | | 12/1992 | Amplatz et al. | 604/281 |
| 5,171,314 A | * | 12/1992 | Dulebohn | 606/113 |
| 5,300,086 A | * | 4/1994 | Gory et al. | 606/200 |
| 5,324,304 A | * | 6/1994 | Rasmussen | 606/200 |
| 5,344,427 A | * | 9/1994 | Cottenceau et al. | 606/200 |
| 5,370,657 A | * | 12/1994 | Irie | 606/200 |
| 5,383,887 A | * | 1/1995 | Nadal | 606/200 |
| 5,413,586 A | * | 5/1995 | Dibie et al. | 606/200 |
| 5,415,630 A | * | 5/1995 | Gory et al. | 606/200 |
| 5,634,942 A | * | 6/1997 | Chevillon et al. | 623/1 |
| 5,649,953 A | * | 7/1997 | Lefebvre | 606/200 |
| 5,681,347 A | * | 10/1997 | Cathcart et al. | 606/200 |
| 5,944,728 A | | 8/1999 | Bates | 606/127 |
| 5,993,474 A | * | 11/1999 | Ouchi | 606/206 |

OTHER PUBLICATIONS

Greenfield et al., "Staging of Fixation and Retrievability of Greenfield Filters", *Journal of Vascular Surgery*, pp. 744–750, Nov. 1994.

Millward, "Temporary and Retrievable Inferior Vena Cava Filters: Current Status[1]", *JVIR*, vol. 9, No. 3, pp. 381–387, May–Jun. 1998.

"Gunther Tulip Vena Cava Filter Set", brochure, 10 pgs.

"Tricep™ Hooked–Prong Grasping Forceps", Microvasive Boston Scientific Corporation brochure, 1 pg.

* cited by examiner

*Primary Examiner*—Cary E. O'Connor
(74) *Attorney, Agent, or Firm*—Crompton, Seager & Tufte LLC

(57) ABSTRACT

A device for removing a thrombus filter from a blood vessel is disclosed. A device in accordance with the present invention includes a shaft having a proximal end, a distal end, and a lumen extending therethrough, a wire having a first end and a second end, the wire being partially disposed within the lumen of the shaft, a portion of the wire extending beyond the distal end of the shaft and forming a loop, and a portion of the wire extending beyond the proximal end of the shaft.

17 Claims, 3 Drawing Sheets

RETRIEVAL DEVICES FOR VENA CAVA FILTER

CROSS REFERENCE TO RELATED APPLICATION

The present application claims the benefit of U.S. Provisional Application Serial No. 60/101,616, filed Sept. 24, 1998.

BACKGROUND OF THE INVENTION

The present invention pertains to the field of intra vena cava filters. In particular, the present invention pertains to the retrieval of intra vena cava filters.

Intra vena cava filters are commonly implanted either temporarily or permanently in patients at risk for blood clotting.

SUMMARY OF THE INVENTION

The present invention pertains to an intra vena cava filter implantable temporarily or permanently, and methods for removal thereof. The filter includes struts having sharpened tips which engage the wall of the vein or inner surface of another organ to provide positional stability of the filter. The method in accordance with the present invention preferably includes the steps of further stabilizing the filter, compressing the struts and shielding the sharpened tips of the struts for subsequent removal of the filter.

DETAILED DESCRIPTION OF THE INVENTION

Figure 1:
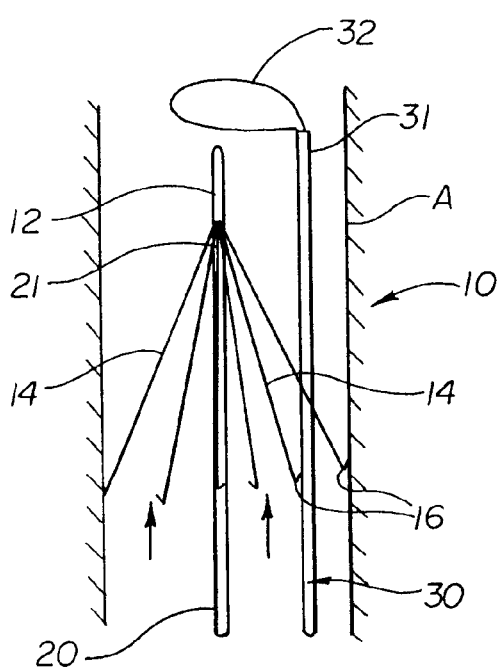
FIG. 1 is a view of an intra vena cava filter and a removal device disposed within a vessel.

Referring now to the drawings wherein like reference numerals refer to like elements throughout the several views, FIG. 1 is a side view of a filter 10 disposed within a vessel or vena cava A. Filter 10 includes a hub 12 from which extends a plurality of struts 14. Each strut preferably includes bends along its length to catch thrombus which flows through vessel A in the direction of the arrows. The end of each strut preferably includes a barb 16 for engagement with the vessel wall to stabilize filter 10 within vessel A. In particular, filter 10 can be a prior art filter such as the Greenfield™ filter made by Medi-Tech (Watertown, Mass.). Filter 10 can be placed within vessel A by way of a jugular vein access point or other intravascular route as known to those skilled in the art.

It is anticipated that the filter disclosed herein can be placed permanently in the vena cava or other organ, as well as being placed temporarily. The tools and methods for removing the filter disclosed herein would likely be used within several weeks after implantation of the filter prior to endothelial growth over a portion of the filter making removal substantially more difficult.

Also shown in FIG. 1 is a stabilizer 20. Stabilizer 20 includes a proximal end and a distal end 21. Stabilizer 20 can be advanced to filter 10 by way of a femoral vein access point. Stabilizer 20 is preferably made from a substantially rigid biocompatible material such as, for example, a stainless steel hypotube or steerable catheter.

Disposed adjacent filter 10 in FIG. 1 is a removal device 30. Removal device 30, like stabilizer 20, can be advanced to filter 10 by way of a femoral vein access point. Removal device 30 preferably includes an elongate shaft having a proximal end (not shown) and a distal end. Shaft 30 is preferably formed from a substantially rigid, biocompatible material such as a stainless steel hypotube. Extending from the distal end of shaft 31 is a wire loop 32. Wire loop 32 is preferably formed from a NiTi alloy such as Nitinol. The wire forming loop 32 preferably extends through shaft 31 to its proximal end such that a physician can draw loop 32 into shaft 31. The wire forming loop 32 is preferably heat set or mechanically biased to bend approximately perpendicularly to shaft 31, as shown in FIG. 1, as it is advanced from the distal end of shaft 31 in vessel A.

Figure 2:
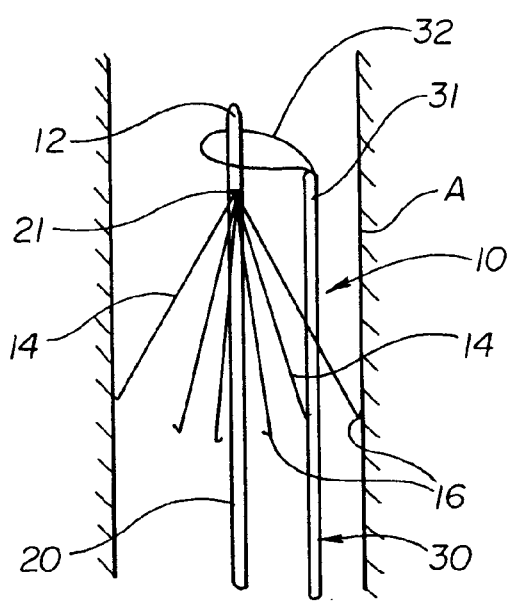
FIG. 2 is a view of the filter of FIG. 1 and the removal device in a subsequent position in the process of removal.
Figure 3:
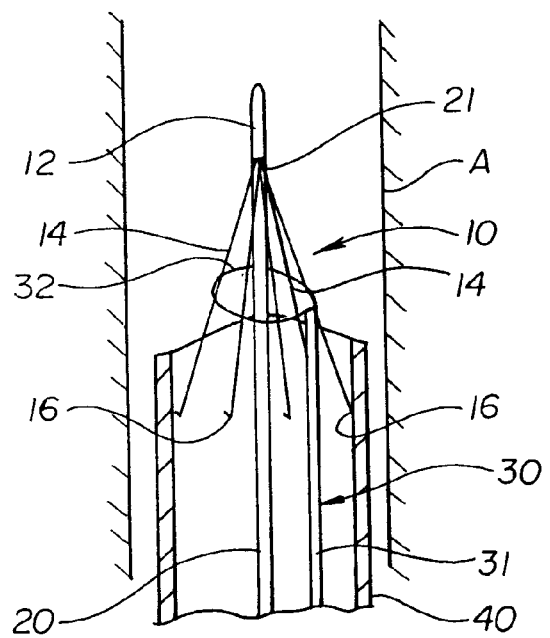
FIG. 3 is a view of the filter of FIG. 1 and the removal device in a position subsequent to that shown in FIG. 2 in the process of removal.

FIG. 2 is a view of the filter of FIG. 1, wherein loop 32 has been placed around filter 10 by pulling removal device 30 proximally. FIG. 3 is a view of filter 10 of FIG. 1, wherein device 30 has been pulled yet more proximally than shown in FIG. 2, relative to filter 10 and stabilizer 20. By pulling removal device 30 more proximally as shown in FIG. 3, struts 14 are compressed inwardly toward stabilizer 20 such that barbs 16 are withdrawn from the wall of vessel A.

Also shown in FIG. 3, in cross section, is a removal sheath 40. Sheath 40 can be formed of a biocompatible material in a manner similar to, for example, a guide catheter. Sheath 40 can be advanced to filter 10 by way of, for example, a femoral vein access point. As can be seen in FIG. 3, once struts 14 have been compressed sufficiently inward by removal device 30, filter 10 can be withdrawn into sheath 40, and subsequently removed from the patient.

Figure 4:
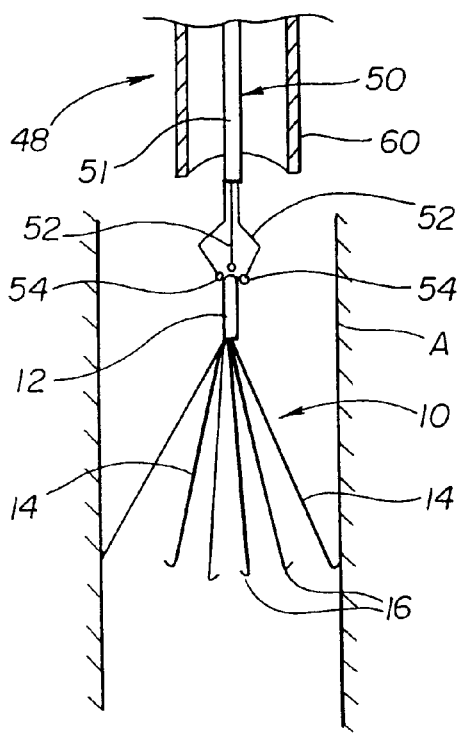
FIG. 4 is a view of the intra vena cava filter of FIG. 1 and an alternate embodiment of a removal device disposed within a vessel.

FIG. 4 is a view of the filter of FIG. 1. A removal device 48 is disposed above filter 10 in FIG. 4. Device 48 includes a stabilizer 50 and a catheter 60. Catheter 60 could be made in a manner similar to a guide catheter. Stabilizer 50 preferably includes a tubular shaft 51 having a proximal end (not shown) and a distal end. Preferably extending between the proximal end and the distal end are elongate members 52 having a distal end extending beyond the distal end of shaft 51. The distal end of members 52 are preferably bent to form a claw as shown. Atraumatic balls 54 can be disposed at the distal end of members 52. Removal device 48 can be placed in the position shown by way of, for example, a jugular vein access point.

Figure 5:
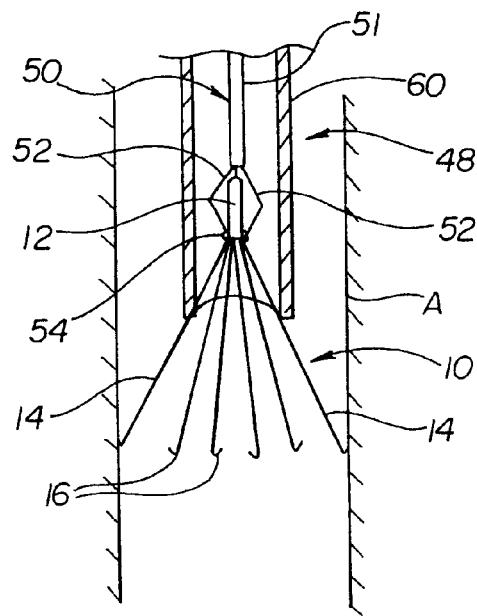
FIG. 5 is a view of the filter of FIG. 4 and the removal device in a subsequent position in the process of removal.

FIG. 5 is a view of the filter of FIG. 4 in which the claw portion of stabilizer 50 has been brought into contact with hub 12. Atraumatic balls 54 are shown engaging a portion of hub 12 to hold filter 10. The claw portion of device 50 can be closed to grasp hub 12 by advancing shaft 51 over members 52 to engage the claw portion forcing balls 54 toward each other. Once filter 10 is grasped by stabilizer 50, catheter 60 can be advanced into engagement with struts 14.

Figure 6:
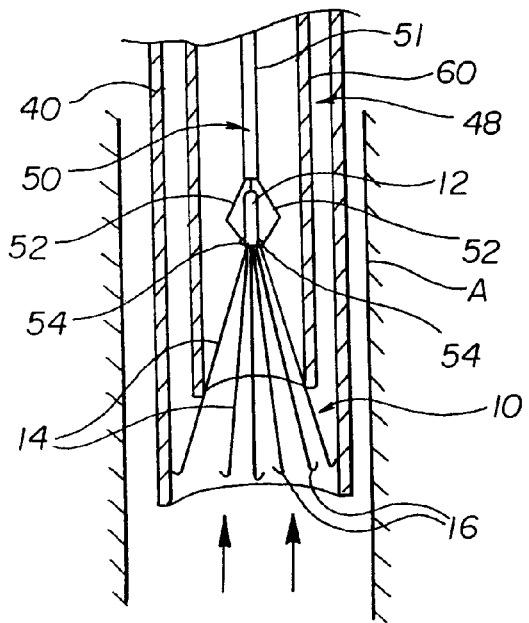
FIG. 6 is a view of the filter of FIG. 4 and the removal device in a position subsequent to that shown in FIG. 5 in the process of removal.

FIG. 6 shows the filter of FIG. 4, wherein catheter 60 has been advanced further than as shown in FIG. 5, to compress struts 14 inwardly and draw tips 16 away from the wall of vessel A. Sheath 40 has been advanced from, for example, a jugular vein access point over the entire filter 10. Sheath 40 shields the vessel wall from tips 16 during subsequent removal of filter 10 in the direction shown by the arrows.

Figure 7:
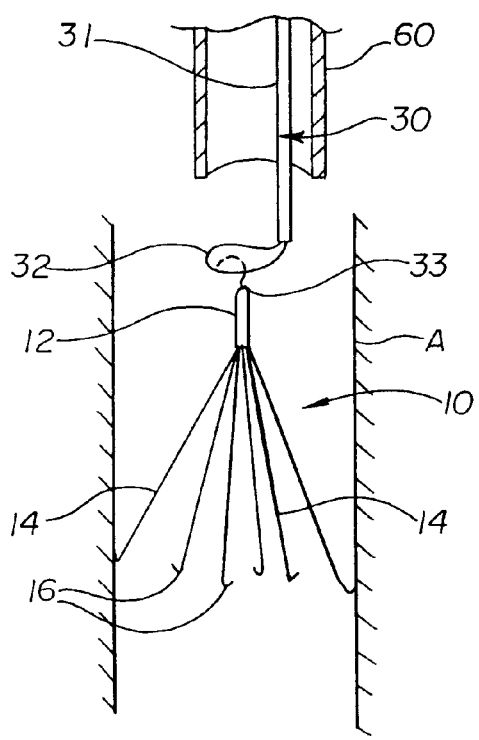
FIG. 7 is a view of the intra vena cava filter of FIG. 1 and yet an alternate embodiment of a removal device disposed within a vessel.

FIG. 7 is a view of the filter of FIG. 1 disposed in vena cava A. Positioned above filter 10 is removal device 30 disposed within catheter 60. Device 30 and catheter 60 are preferably advanced into this position by way of a jugular vein access point.

Figure 8:
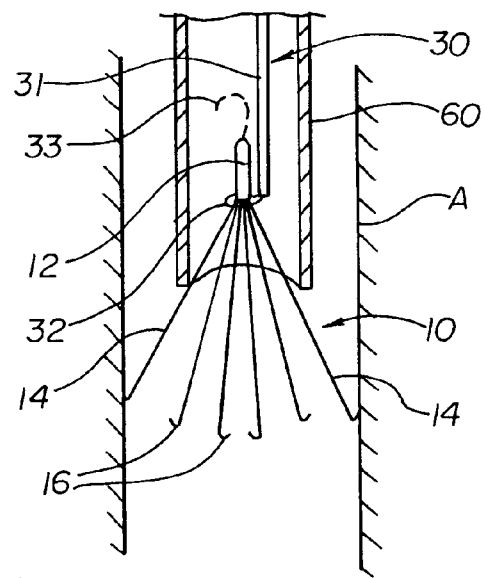
FIG. 8 is a view of the filter of FIG. 7 and the removal device in a subsequent position in the process of removal.

As shown in FIG. 8, loop 32 of device 30 has been placed around a portion of hub 12. Alternatively, hub 12 could include a hook 33 shown in phantom lines, to which loop 32 could be attached. The wire forming loop 32 has been drawn proximally into shaft 31 to tighten loop 32 around hub 12. Catheter 36 has been advanced distally to engage struts 14.

Figure 9:
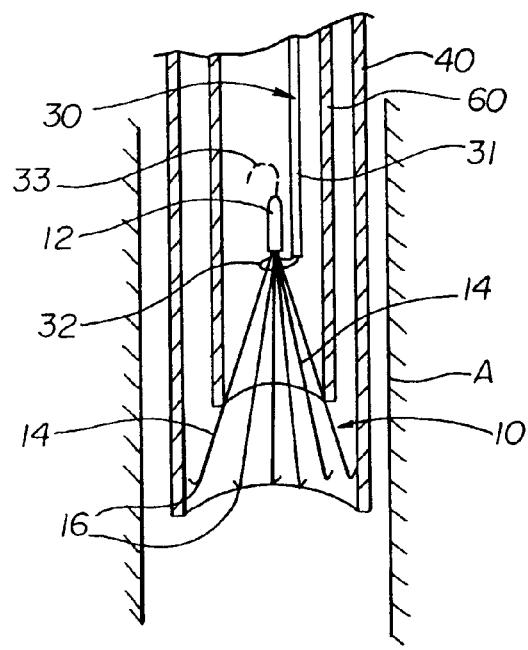
FIG. 9 is a view of the filter of FIG. 1 and the removal device in a position subsequent to that shown in FIG. 8 in the process of removal.

As shown in FIG. 9, catheter 60 has been advanced further relative to device 30 and filter 10 than as shown in FIG. 8. By advancing catheter 60 in this way, struts 14 have been compressed inwardly to disengage tips 16 from the wall of vessel A. Embodiments of the present invention have been envisioned, in which loop 30 is adapted to compress struts 14 inward and disengage tips 16 from the wall of vessel A. Methods in accordance with the present invention have been envisioned in which loop 32 is advanced distally to compress struts 14 inward and disengage tips 16 from the wall of vessel A. Sheath 40 is advanced distally as shown in FIG. 9 to cover filter 10 and shield the vessel wall from tip 16 as filter 10 is subsequently removed.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A device for removing a thrombus filter from a blood vessel, comprising:
   a shaft having a proximal end, a distal end, and a lumen extending therethrough;
   a wire having a first end and a second end;
   the wire being partially disposed within the lumen of the shaft;
   a portion of the wire extending beyond the distal end of the shaft and forming a loop,
   a portion of the wire extending beyond the proximal end of the shaft; and
   a stabilizer disposed generally adjacent and parallel to the shaft, the stabilizer comprising an elongate body having a proximal end and a distal end wherein, the distal end of the elongate body of the stabilizer is adapted to engage the thrombus filter.

2. A device, comprising:
   a sheath having a proximal end, a distal end, and a lumen extending therethrough;
   a shaft disposed within the lumen of the sheath;
   the shaft having a proximal end, a distal end, and a lumen extending therethrough;
   a wire having a first end and a second end;
   the wire being partially disposed within the lumen of the shaft;
   a portion of the wire extending beyond the distal end of the shaft and forming a loop;
   a portion of the wire extending beyond the proximal end of the shaft; and
   a thrombus filter, wherein the loop is configured to surround a portion of the thrombus filter.

3. The device of claim 2, wherein the first end and the second end of the wire extend beyond the proximal end of the shaft.

4. The device of claim 2, wherein the wire is comprised of Nitinol.

5. The device of claim 2, wherein the loop formed by the wire is generally perpendicular to the shaft.

6. The device of claim 2, further including a stabilizer disposed within the lumen of the sheath, the stabilizer comprising an elongate body having a proximal end and a distal end.

7. The device of claim 2, further including a stabilizer disposed within the lumen of the sheath, the stabilizer comprising an elongate body having a proximal end and a distal end, wherein the distal end of the elongate body of the stabilizer is adapted to engage the thrombus filter.

8. The device of claim 2, further including a stabilizer disposed within the lumen of the sheath, the stabilizer comprising an elongate body having a proximal end and a distal end wherein, the elongate body of the stabilizer is longer than the sheath.

9. The device of claim 2, wherein the shaft is longer than the sheath.

10. A device comprising: a catheter having a proximal end, a distal end, and a lumen extending therethrough;
    a shaft disposed within the lumen of the catheter;
    the shaft having a proximal end, a distal end, and a lumen extending therethrough;
    a plurality of elongate members each having a proximal end, and a distal portion terminating at a distal end;
    a portion of each elongate member being disposed within the lumen of the shaft;
    the distal portion of each elongate member extending beyond the distal end of the shaft;
    the distal portion of each elongate member including a plurality of bends such that the distal portions of the elongate members form a claw; and
    a thrombus filter, wherein the claw formed by the distal portions of the elongate members is adapted to engage the thrombus filter.

11. The device of claim 10, wherein the claw formed by the distal portions of the elongate members is disposed about the thrombus filter.

12. The device of claim 10, wherein an atraumatic tip is formed at the distal end of each elongate member.

13. The device of claim 10, wherein an atraumatic ball is disposed at the distal end of each elongate member.

14. The device of claim 10, wherein the proximal end of each elongate member extends beyond the proximal end of the shaft.

15. The device of claim 10, further including a rod disposed within the lumen of the shaft, the rod having a distal end and a proximal end, and wherein the proximal end of each elongate member is fixed to the distal end of the rod.

16. The device of claim 10, further including a rod disposed within the lumen of the shaft, the rod having a distal end and a proximal end, the proximal end of each elongate member being fixed to the distal end of the rod, and the proximal end of the rod extending beyond the proximal end of the shaft.

17. The device of claim 10, wherein each elongate member is comprised of Nitinol.

* * * * *